(12) United States Patent
Meyer

(10) Patent No.: US 7,618,513 B2
(45) Date of Patent: **\*Nov. 17, 2009**

(54) WEB STABILIZATION ON A SLIP AND CUT APPLICATOR

(75) Inventor: Thomas C. Meyer, Elkhart Lake, WI (US)

(73) Assignee: Curt G. Joa, Inc., Sheboygan Falls, WI (US)

(\*) Notice: Subject to any disclaimer, the term of this patent is extended or adjusted under 35 U.S.C. 154(b) by 273 days.

This patent is subject to a terminal disclaimer.

(21) Appl. No.: 11/141,633

(22) Filed: May 31, 2005

(65) Prior Publication Data

US 2006/0266466 A1 Nov. 30, 2006

(51) Int. Cl.
*B32B 37/00* (2006.01)
(52) U.S. Cl. .................. 156/285; 156/265; 156/517
(58) Field of Classification Search .............. 156/265, 156/285, 250, 516, 517, 519, 520, 521, 555, 156/582; 269/21; 34/453, 458, 581
See application file for complete search history.

(56) References Cited

U.S. PATENT DOCUMENTS

| | | | |
|---|---|---|---|
| 135,145 A | 1/1873 | Murphy |
| 293,353 A | 2/1884 | Purvis |
| 312,257 A | 2/1885 | Cotton et al. |
| 410,123 A | 8/1889 | Stilwell |
| 432,742 A | 7/1890 | Stanley |
| 643,821 A | 2/1900 | Howlett |
| 1,393,524 A | 10/1921 | Grupe |
| 1,605,842 A | 11/1926 | Jones |
| 1,686,595 A | 10/1928 | Belluche |
| 1,957,651 A | 5/1934 | Joa |
| 2,009,857 A | 7/1935 | Potdevin |
| 2,054,832 A | 9/1936 | Potdevin |
| 2,117,432 A | 5/1938 | Linscott |
| 2,128,746 A | 8/1938 | Joa |
| 2,131,808 A | 10/1938 | Joa |
| 2,164,408 A | 7/1939 | Joa |
| 2,167,179 A | 7/1939 | Joa |

(Continued)

FOREIGN PATENT DOCUMENTS

BE 1007854 11/1995

(Continued)

OTHER PUBLICATIONS

Reciprocating Mechanisms, Ingenious Mechanisms for Designers and Inventors, Franklin Jones vol. 1.

*Primary Examiner*—James Sells
(74) *Attorney, Agent, or Firm*—Ryan Kromholz & Manion S.C.

(57) ABSTRACT

This invention proposes a new, improved method and apparatus for applying web segments to a traveling web. Ears, or wings, are placed on a running web of disposable diapers. Because these webs are often asymmetrical or otherwise incompatible with the principle of slipping over the surface of a moving vacuum roll, the webs may float from side to side or otherwise be drawn out of square by asymmetrical forces. A vacuum groove is provided on a vacuum roll to counter these effects. Alternatively, a ridge with vacuum about the ridge is provided, also to pull a machine direction line of material into the groove or over the ridge, thereby giving the web some degree of cross-directional stability.

5 Claims, 3 Drawing Sheets

U.S. PATENT DOCUMENTS

| | | |
|---|---|---|
| 2,171,741 A | 9/1939 | Cohn et al. |
| 2,213,431 A | 9/1940 | Joa |
| 2,254,290 A | 9/1941 | Joa |
| 2,254,291 A | 9/1941 | Joa |
| 2,282,477 A | 5/1942 | Joa |
| 2,286,096 A | 6/1942 | Joa |
| 2,296,931 A | 9/1942 | Joa |
| 2,304,571 A | 12/1942 | Joa |
| 2,324,930 A | 7/1943 | Joa |
| 2,345,937 A | 4/1944 | Joa |
| 2,466,240 A | 4/1949 | Joa |
| 2,481,929 A | 9/1949 | Joa |
| 2,510,229 A | 6/1950 | Joa |
| 2,540,844 A | 2/1951 | Strauss |
| 2,584,002 A | 1/1952 | Elser et al. |
| 2,591,359 A | 4/1952 | Joa |
| 2,618,816 A | 11/1952 | Joa |
| 2,702,406 A | 2/1955 | Reed |
| 2,721,554 A | 10/1955 | Joa |
| 2,730,144 A | 1/1956 | Joa |
| 2,772,611 A | 12/1956 | Heywood |
| 2,780,253 A | 2/1957 | Joa |
| 2,785,609 A | 3/1957 | Billeb |
| 2,811,905 A | 11/1957 | Kennedy, Jr. |
| 2,839,059 A | 6/1958 | Joa |
| 2,842,169 A | 7/1958 | Joa |
| 2,851,934 A | 9/1958 | Heywood |
| 2,875,724 A | 3/1959 | Joa |
| 2,913,862 A | 11/1959 | Sabee |
| 2,939,461 A | 6/1960 | Joa |
| 2,960,143 A | 11/1960 | Joa |
| 2,990,081 A | 6/1961 | Neui et al. |
| 2,991,739 A | 7/1961 | Joa |
| 3,016,207 A | 1/1962 | Comstock |
| 3,016,582 A | 1/1962 | Joa |
| 3,017,795 A | 1/1962 | Joa |
| 3,020,687 A | 2/1962 | Joa |
| 3,021,135 A | 2/1962 | Joa |
| 3,024,957 A | 3/1962 | Pinto |
| 3,053,427 A | 9/1962 | Wasserman |
| 3,054,516 A | 9/1962 | Joa |
| 3,069,982 A | 12/1962 | Heywood et al. |
| 3,086,253 A | 4/1963 | Joa |
| 3,087,689 A | 4/1963 | Heim |
| 3,091,408 A | 5/1963 | Schoeneman |
| 3,114,994 A | 12/1963 | Joa |
| 3,122,293 A | 2/1964 | Joa |
| 3,128,206 A | 4/1964 | Dungler |
| 3,203,419 A | 8/1965 | Joa |
| 3,230,955 A | 1/1966 | Joa et al. |
| 3,268,954 A | 8/1966 | Joa |
| 3,288,037 A | 11/1966 | Burnett |
| 3,289,254 A | 12/1966 | Joa |
| 3,291,131 A | 12/1966 | Joa |
| 3,301,114 A | 1/1967 | Joa |
| 3,322,589 A | 5/1967 | Joa |
| 3,342,184 A | 9/1967 | Joa |
| 3,356,092 A | 12/1967 | Joa |
| 3,360,103 A | 12/1967 | Johnson |
| 3,363,847 A | 1/1968 | Joa |
| 3,391,777 A | 7/1968 | Joa |
| 3,454,442 A | 7/1969 | Heller Jr. |
| 3,470,848 A | 10/1969 | Dreher |
| 3,484,275 A | 12/1969 | Lewicki, Jr. |
| 3,502,322 A | 3/1970 | Cran |
| 3,521,639 A | 7/1970 | Joa |
| 3,526,563 A | 9/1970 | Schott, Jr. |
| 3,538,551 A | 11/1970 | Joa |
| 3,540,641 A | 11/1970 | Besnyo et al. |
| 3,575,170 A | 4/1971 | Clark |
| 3,607,578 A | 9/1971 | Berg et al. |
| 3,635,462 A | 1/1972 | Joa |
| 3,656,741 A | 4/1972 | Macke et al. |
| 3,666,611 A | 5/1972 | Joa |
| 3,673,021 A | 6/1972 | Joa |
| 3,685,818 A | 8/1972 | Burger |
| 3,728,191 A | 4/1973 | Wierzba et al. |
| 3,751,224 A | 8/1973 | Wackerle |
| 3,772,120 A | 11/1973 | Radzins |
| 3,796,360 A | 3/1974 | Alexeff |
| 3,816,210 A | 6/1974 | Aoko et al. |
| 3,847,710 A | 11/1974 | Blomqvist et al. |
| 3,854,917 A | 12/1974 | McKinney et al. |
| 3,883,389 A | 5/1975 | Schott, Jr. |
| 3,888,400 A | 6/1975 | Wiig |
| 3,903,768 A | 9/1975 | Amberg et al. |
| 3,904,147 A | 9/1975 | Taitel et al. |
| 3,918,698 A | 11/1975 | Coast |
| 3,960,646 A | 6/1976 | Wiedamann |
| 3,991,994 A * | 11/1976 | Farish ........................ 493/430 |
| 4,002,005 A | 1/1977 | Mueller et al. |
| 4,003,298 A | 1/1977 | Schott, Jr. |
| 4,009,814 A | 3/1977 | Singh |
| 4,009,815 A | 3/1977 | Ericson et al. |
| 4,053,150 A | 10/1977 | Lane |
| 4,056,919 A | 11/1977 | Hirsch |
| 4,081,301 A | 3/1978 | Buell |
| 4,090,516 A | 5/1978 | Schaar |
| 4,094,319 A | 6/1978 | Joa |
| 4,103,595 A | 8/1978 | Corse |
| 4,106,974 A | 8/1978 | Hirsch |
| 4,108,584 A | 8/1978 | Radzins et al. |
| 4,136,535 A | 1/1979 | Audas |
| 4,141,193 A | 2/1979 | Joa |
| 4,141,509 A | 2/1979 | Radzins |
| 4,142,626 A | 3/1979 | Bradley |
| 4,157,934 A | 6/1979 | Ryan et al. |
| 4,165,666 A | 8/1979 | Johnson et al. |
| 4,168,776 A | 9/1979 | Hoeboer |
| 4,171,239 A | 10/1979 | Hirsch et al. |
| 4,205,679 A | 6/1980 | Repke et al. |
| 4,208,230 A | 6/1980 | Magarian |
| 4,213,356 A | 7/1980 | Armitage |
| 4,215,827 A | 8/1980 | Roberts et al. |
| 4,222,533 A | 9/1980 | Pongracz |
| 4,223,822 A | 9/1980 | Clitheroe |
| 4,231,129 A | 11/1980 | Winch |
| 4,236,955 A | 12/1980 | Prittie |
| 4,275,510 A | 6/1981 | George |
| 4,284,454 A | 8/1981 | Joa |
| 4,307,800 A | 12/1981 | Joa |
| 4,316,756 A | 2/1982 | Wilson |
| 4,342,206 A | 8/1982 | Rommel |
| 4,364,787 A | 12/1982 | Radzins |
| 4,374,576 A | 2/1983 | Ryan |
| 4,379,008 A | 4/1983 | Gross et al. |
| 4,394,898 A | 7/1983 | Campbell |
| 4,411,721 A | 10/1983 | Wishart |
| 4,452,597 A | 6/1984 | Achelpohl |
| 4,492,608 A | 1/1985 | Hirsch et al. |
| 4,501,098 A | 2/1985 | Gregory |
| 4,508,528 A | 4/1985 | Hirsch et al. |
| 4,522,853 A | 6/1985 | Szonn et al. |
| 4,551,191 A | 11/1985 | Kock et al. |
| 4,586,199 A | 5/1986 | Birring |
| 4,589,945 A | 5/1986 | Polit |
| 4,603,800 A | 8/1986 | Focke et al. |
| 4,614,076 A | 9/1986 | Rathemacher |
| 4,619,357 A | 10/1986 | Radzins et al. |
| 4,634,482 A | 1/1987 | Lammers |
| 4,641,381 A | 2/1987 | Heran et al. |
| 4,642,150 A | 2/1987 | Stemmler |
| 4,642,839 A | 2/1987 | Urban |
| 4,650,530 A | 3/1987 | Mahoney et al. |

| | | | | | | |
|---|---|---|---|---|---|---|
| 4,663,220 A | 5/1987 | Wisneski et al. | | 5,449,353 A | 9/1995 | Watanabe et al. |
| 4,672,705 A | 6/1987 | Bors et al. | | 5,464,401 A | 11/1995 | Hasse et al. |
| 4,675,062 A | 6/1987 | Instance | | 5,486,253 A | 1/1996 | Otruba |
| 4,693,056 A | 9/1987 | Raszewski | | 5,494,622 A | 2/1996 | Heath et al. |
| 4,701,239 A | 10/1987 | Craig | | 5,531,850 A | 7/1996 | Herrmann |
| 4,726,874 A | 2/1988 | Van Vilet | | 5,540,647 A | 7/1996 | Weiermann et al. |
| 4,726,876 A | 2/1988 | Tomsovic et al. | | 5,545,275 A | 8/1996 | Herrin et al. |
| 4,743,241 A | 5/1988 | Igaue et al. | | 5,545,285 A | 8/1996 | Johnson |
| 4,751,997 A | 6/1988 | Hirsch | | 5,552,013 A | 9/1996 | Ehlert et al. |
| 4,753,429 A | 6/1988 | Inrvine et al. | | 5,556,360 A | 9/1996 | Kober et al. |
| 4,756,141 A | 7/1988 | Hirsch et al. | | 5,556,504 A | 9/1996 | Rajala et al. |
| 4,764,325 A | 8/1988 | Angstadt | | 5,560,793 A | 10/1996 | Ruscher et al. |
| 4,765,780 A | 8/1988 | Angstadt | | 5,602,747 A | 2/1997 | Rajala |
| 4,776,920 A | 10/1988 | Ryan | | 5,624,420 A | 4/1997 | Bridges et al. |
| 4,777,513 A | 10/1988 | Nelson | | 5,624,428 A | 4/1997 | Sauer |
| 4,782,647 A | 11/1988 | Williams et al. | | 5,628,738 A | 5/1997 | Suekane |
| 4,785,986 A | 11/1988 | Daane et al. | | 5,634,917 A | 6/1997 | Fujioka et al. |
| 4,795,510 A | 1/1989 | Wittrock et al. | | 5,643,165 A | 7/1997 | Klekamp |
| 4,801,345 A | 1/1989 | Dussaud et al. | | 5,643,396 A | 7/1997 | Rajala et al. |
| 4,802,570 A | 2/1989 | Hirsch et al. | | 5,645,543 A | 7/1997 | Nomura et al. |
| 4,840,609 A | 6/1989 | Jones et al. | | 5,659,229 A | 8/1997 | Rajala |
| 4,845,964 A | 7/1989 | Bors et al. | | 5,660,657 A | 8/1997 | Rajala et al. |
| 4,864,802 A | 9/1989 | D'Angelo | | 5,660,665 A | 8/1997 | Jalonen |
| 4,880,102 A | 11/1989 | Indrebo | | 5,683,376 A | 11/1997 | Kato et al. |
| 4,888,231 A | 12/1989 | Angstadt | | RE35,687 E | 12/1997 | Igaue et al. |
| 4,892,536 A | 1/1990 | Des Marais et al. | | 5,693,165 A | 12/1997 | Schmitz |
| 4,904,440 A | 2/1990 | Angstadt | | 5,699,653 A | 12/1997 | Hartman et al. |
| 4,908,175 A | 3/1990 | Angstadt | | 5,707,470 A | 1/1998 | Rajala et al. |
| 4,909,019 A | 3/1990 | Delacretaz et al. | | 5,711,832 A | 1/1998 | Glaug et al. |
| 4,925,520 A | 5/1990 | Beaudoin et al. | | 5,725,518 A | 3/1998 | Coates |
| 4,927,322 A | 5/1990 | Schweizer et al. | | 5,745,922 A | 5/1998 | Rajala et al. |
| 4,927,582 A | 5/1990 | Bryson | | 5,746,869 A | 5/1998 | Hayden et al. |
| 4,937,887 A | 7/1990 | Schreiner | | 5,749,989 A | 5/1998 | Linman et al. |
| 4,963,072 A | 10/1990 | Miley et al. | | 5,788,797 A | 8/1998 | Herrin et al. |
| 4,987,940 A | 1/1991 | Straub et al. | | 5,817,199 A | 10/1998 | Brennecke et al. |
| 4,994,010 A | 2/1991 | Doderer-Winkler | | 5,829,164 A * | 11/1998 | Kotitschke .................. 34/453 |
| 5,000,806 A | 3/1991 | Merkatoris et al. | | 5,836,931 A | 11/1998 | Toyoda et al. |
| 5,021,111 A | 6/1991 | Swenson | | 5,858,012 A | 1/1999 | Yamaki et al. |
| 5,025,910 A | 6/1991 | Lasure et al. | | 5,865,393 A | 2/1999 | Kreft et al. |
| 5,045,039 A | 9/1991 | Bay | | 5,868,727 A | 2/1999 | Barr et al. |
| 5,062,597 A | 11/1991 | Martin et al. | | 5,876,027 A | 3/1999 | Fukui et al. |
| 5,064,179 A | 11/1991 | Martin | | 5,876,792 A | 3/1999 | Caldwell |
| 5,080,741 A | 1/1992 | Nomura et al. | | 5,879,500 A | 3/1999 | Herrin et al. |
| 5,094,658 A | 3/1992 | Smithe et al. | | 5,902,431 A | 5/1999 | Wilkinson et al. |
| 5,096,532 A | 3/1992 | Neuwirth et al. | | 5,932,039 A | 8/1999 | Popp et al. |
| 5,108,017 A | 4/1992 | Adamski et al. | | 5,938,193 A | 8/1999 | Bluemle et al. |
| 5,109,767 A | 5/1992 | Nyfeler et al. | | 5,964,970 A | 10/1999 | Woolwine et al. |
| 5,110,403 A | 5/1992 | Ehlert | | 6,036,805 A | 3/2000 | McNichols |
| 5,127,981 A | 7/1992 | Straub et al. | | 6,043,836 A | 3/2000 | Kerr et al. |
| 5,131,525 A | 7/1992 | Musschoot | | 6,050,517 A | 4/2000 | Dobrescu et al. |
| 5,147,487 A | 9/1992 | Nomura et al. | | 6,074,110 A | 6/2000 | Verlinden et al. |
| 5,163,594 A | 11/1992 | Meyer | | 6,076,442 A | 6/2000 | Arterburn et al. |
| 5,171,239 A | 12/1992 | Igaue et al. | | 6,098,249 A | 8/2000 | Toney et al. |
| 5,176,244 A | 1/1993 | Radzins et al. | | 6,123,792 A | 9/2000 | Samida et al. |
| 5,183,252 A | 2/1993 | Wolber et al. | | 6,171,432 B1 | 1/2001 | Brisebois et al. |
| 5,188,627 A | 2/1993 | Igaue et al. | | 6,183,576 B1 | 2/2001 | Couillard et al. |
| 5,195,684 A | 3/1993 | Radzins | | 6,210,386 B1 | 4/2001 | Inoue |
| 5,203,043 A | 4/1993 | Riedel | | 6,212,859 B1 | 4/2001 | Bielik, Jr. et al. |
| 5,213,645 A | 5/1993 | Nomura et al. | | 6,250,048 B1 | 6/2001 | Linkiewicz |
| 5,223,069 A | 6/1993 | Tokuno et al. | | 6,264,784 B1 | 7/2001 | Menard et al. |
| 5,226,992 A | 7/1993 | Morman | | 6,276,421 B1 | 8/2001 | Valenti et al. |
| 5,246,433 A | 9/1993 | Hasse et al. | | 6,306,122 B1 | 10/2001 | Narawa et al. |
| 5,267,933 A | 12/1993 | Precoma | | 6,309,336 B1 | 10/2001 | Muessig et al. |
| 5,308,345 A | 5/1994 | Herrin | | 6,312,420 B1 | 11/2001 | Sasaki et al. |
| 5,328,438 A | 7/1994 | Crowley | | 6,314,333 B1 | 11/2001 | Rajala et al. |
| 5,340,424 A | 8/1994 | Matsushita | | 6,315,022 B1 | 11/2001 | Herrin et al. |
| 5,368,893 A | 11/1994 | Sommer et al. | | 6,336,921 B1 | 1/2002 | Kato et al. |
| 5,407,513 A | 4/1995 | Hayden et al. | | 6,358,350 B1 | 3/2002 | Glaug et al. |
| 5,415,649 A | 5/1995 | Watanabe et al. | | 6,369,291 B1 | 4/2002 | Uchimoto et al. |
| 5,421,924 A | 6/1995 | Ziegelhoffer et al. | | 6,375,769 B1 | 4/2002 | Quereshi et al. |
| 5,424,025 A | 6/1995 | Hanschen et al. | | 6,391,013 B1 | 5/2002 | Suzuki et al. |
| 5,429,576 A | 7/1995 | Doderer-Winkler | | 6,416,697 B1 | 7/2002 | Venturino et al. |
| 5,435,802 A | 7/1995 | Kober | | 6,443,389 B1 | 9/2002 | Palone |

| | | |
|---|---|---|
| 6,446,795 B1 | 9/2002 | Allen et al. |
| 6,473,669 B2 | 10/2002 | Rajala et al. |
| 6,475,325 B1 | 11/2002 | Parrish et al. |
| 6,478,786 B1 | 11/2002 | Gloug et al. |
| 6,482,278 B1 | 11/2002 | McCabe et al. |
| 6,494,244 B2 | 12/2002 | Parrish et al. |
| 6,521,320 B2 | 2/2003 | McCabe et al. |
| 6,524,423 B1 | 2/2003 | Hilt et al. |
| 6,551,228 B1 | 4/2003 | Richards |
| 6,551,430 B1 | 4/2003 | Glaug et al. |
| 6,554,815 B1 | 4/2003 | Umebayashi |
| 6,572,520 B2 | 6/2003 | Blumle |
| 6,581,517 B1 | 6/2003 | Becker et al. |
| 6,596,108 B2 | 7/2003 | McCabe |
| 6,605,172 B1 | 8/2003 | Anderson et al. |
| 6,605,173 B2 | 8/2003 | Glaug et al. |
| 6,637,583 B1 | 10/2003 | Andersson |
| 6,648,122 B1 | 11/2003 | Hirsch et al. |
| 6,649,010 B2 * | 11/2003 | Parrish et al. .............. 156/265 |
| 6,659,150 B1 | 12/2003 | Perkins et al. |
| 6,659,991 B2 | 12/2003 | Suckane |
| 6,675,552 B2 | 1/2004 | Kunz et al. |
| 6,684,925 B2 | 2/2004 | Nagate et al. |
| 6,743,324 B2 | 6/2004 | Hargett et al. |
| 6,766,817 B2 | 7/2004 | da Silva |
| D497,991 S | 11/2004 | Otsubo et al. |
| 6,820,671 B2 | 11/2004 | Calvert |
| 6,837,840 B2 | 1/2005 | Yonekawa et al. |
| 6,840,616 B2 | 1/2005 | Summers |
| 6,852,186 B1 | 2/2005 | Matsuda et al. |
| 6,875,202 B2 | 4/2005 | Kumasaka et al. |
| 6,893,528 B2 | 5/2005 | Middelstadt et al. |
| 6,918,404 B2 | 7/2005 | Dias da Silva |
| 6,978,486 B2 | 12/2005 | Zhou et al. |
| 7,066,586 B2 | 6/2006 | da Silva |
| 7,077,393 B2 | 7/2006 | Ishida |
| 7,214,174 B2 | 5/2007 | Allen et al. |
| 7,247,219 B2 | 7/2007 | O'Dowd |
| 2001/0012813 A1 | 8/2001 | Bluemle |
| 2001/0017181 A1 | 8/2001 | Otruba et al. |
| 2002/0046802 A1 | 4/2002 | Tachibana et al. |
| 2002/0059013 A1 | 5/2002 | Rajala et al. |
| 2003/0000620 A1 | 1/2003 | Herrin et al. |
| 2003/0015209 A1 | 1/2003 | Gingras et al. |
| 2003/0052148 A1 | 3/2003 | Rajala et al. |
| 2003/0066585 A1 | 4/2003 | McCabe |
| 2003/0083638 A1 | 5/2003 | Malee |
| 2003/0084984 A1 | 5/2003 | Glaug et al. |
| 2003/0089447 A1 | 5/2003 | Molee et al. |
| 2003/0135189 A1 | 7/2003 | Umebayashi |
| 2004/0007328 A1 * | 1/2004 | Popp et al. ................. 156/494 |
| 2004/0016500 A1 | 1/2004 | Tachibana et al. |
| 2004/0112517 A1 * | 6/2004 | Groves et al. .............. 156/264 |
| 2004/0140047 A1 * | 7/2004 | Sato et al. .................. 156/205 |
| 2004/0164482 A1 | 8/2004 | Edinger |
| 2005/0000628 A1 | 1/2005 | Norrley |
| 2005/0196538 A1 | 9/2005 | Sommer et al. |
| 2005/0230056 A1 | 10/2005 | Meyer et al. |
| 2005/0230449 A1 | 10/2005 | Meyer et al. |
| 2005/0233881 A1 | 10/2005 | Meyer |
| 2005/0234412 A1 | 10/2005 | Andrews et al. |
| 2005/0257881 A1 | 11/2005 | Coose et al. |
| 2005/0275148 A1 | 12/2005 | Beaudoin et al. |
| 2006/0021300 A1 | 2/2006 | Tada et al. |
| 2006/0137298 A1 | 6/2006 | Oshita et al. |
| 2006/0224137 A1 | 10/2006 | McCabe et al. |
| 2006/0265867 A1 | 11/2006 | Schaap |
| 2007/0074953 A1 | 4/2007 | McCabe |

FOREIGN PATENT DOCUMENTS

| | | |
|---|---|---|
| CA | 1146129 | 5/1983 |
| CA | 1153345 | 9/1983 |
| CA | 1190078 | 7/1985 |
| CA | 1210744 | 9/1986 |
| CA | 1212132 | 9/1986 |
| CA | 1236056 | 5/1988 |
| CA | 1249102 | 1/1989 |
| CA | 1292201 | 11/1991 |
| CA | 1307244 | 9/1992 |
| CA | 1308015 | 9/1992 |
| CA | 1310342 | 11/1992 |
| CA | 2023816 | 3/1994 |
| CA | 2404154 | 10/2001 |
| CA | 2541194 | 1/2006 |
| CA | 2559517 | 5/2007 |
| DE | 102006047280 | 4/2007 |
| EP | 0044206 | 1/1982 |
| EP | 0048011 | 3/1982 |
| EP | 0089106 | 9/1983 |
| EP | 0206208 | 12/1986 |
| EP | 0304140 | 8/1987 |
| EP | 0439897 | 2/1990 |
| EP | 0455231 | 11/1991 |
| EP | 510251 | 10/1992 |
| EP | 0652175 | 5/1995 |
| EP | 0811473 | 12/1997 |
| EP | 0901780 | 3/1999 |
| EP | 990588 | 4/2000 |
| EP | 1132325 | 9/2001 |
| EP | 1272347 | 1/2003 |
| EP | 1571249 | 9/2005 |
| EP | 1619008 | 1/2006 |
| EP | 1707168 | 4/2006 |
| ES | 509706 | 11/1982 |
| ES | 520559 | 12/1983 |
| ES | 296211 | 12/1987 |
| FR | 2255961 | 7/1975 |
| FR | 2891811 | 4/2007 |
| GB | 191101501 | 7/1911 |
| GB | 439897 | 12/1935 |
| GB | 856389 | 12/1960 |
| GB | 941073 | 11/1963 |
| GB | 1096373 | 12/1967 |
| GB | 1126539 | 9/1968 |
| GB | 1346329 | 2/1974 |
| GB | 1412812 | 11/1975 |
| GB | 2045298 | 10/1980 |
| GB | 2288316 | 10/1995 |
| JP | 428364 | 1/1992 |
| JP | 542180 | 2/1993 |
| JP | 576566 | 3/1993 |
| JP | 626160 | 2/1994 |
| JP | 626161 | 2/1994 |
| JP | 6197925 | 7/1994 |
| JP | 10035621 | 2/1998 |
| JP | 10-277091 | 10/1998 |
| SE | 0602047 | 5/2007 |
| WO | WO9747265 | 12/1997 |
| WO | WO 9747810 | 12/1997 |
| WO | WO9907319 | 2/1999 |
| WO | WO9913813 | 3/1999 |
| WO | WO9965437 | 12/1999 |
| WO | WO0143682 | 6/2001 |
| WO | WO0172237 | 10/2001 |
| WO | WO2005075163 | 1/2005 |

* cited by examiner

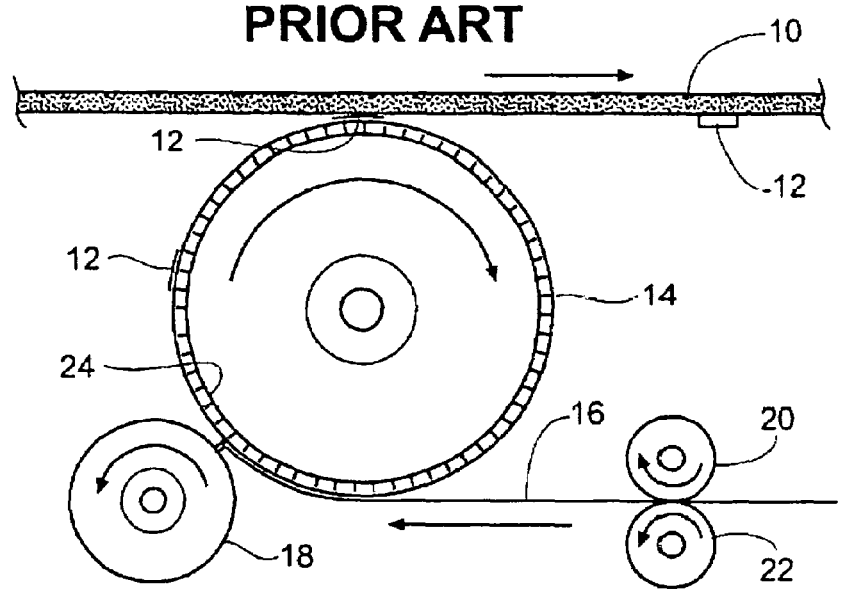
PRIOR ART
*Fig. 1*
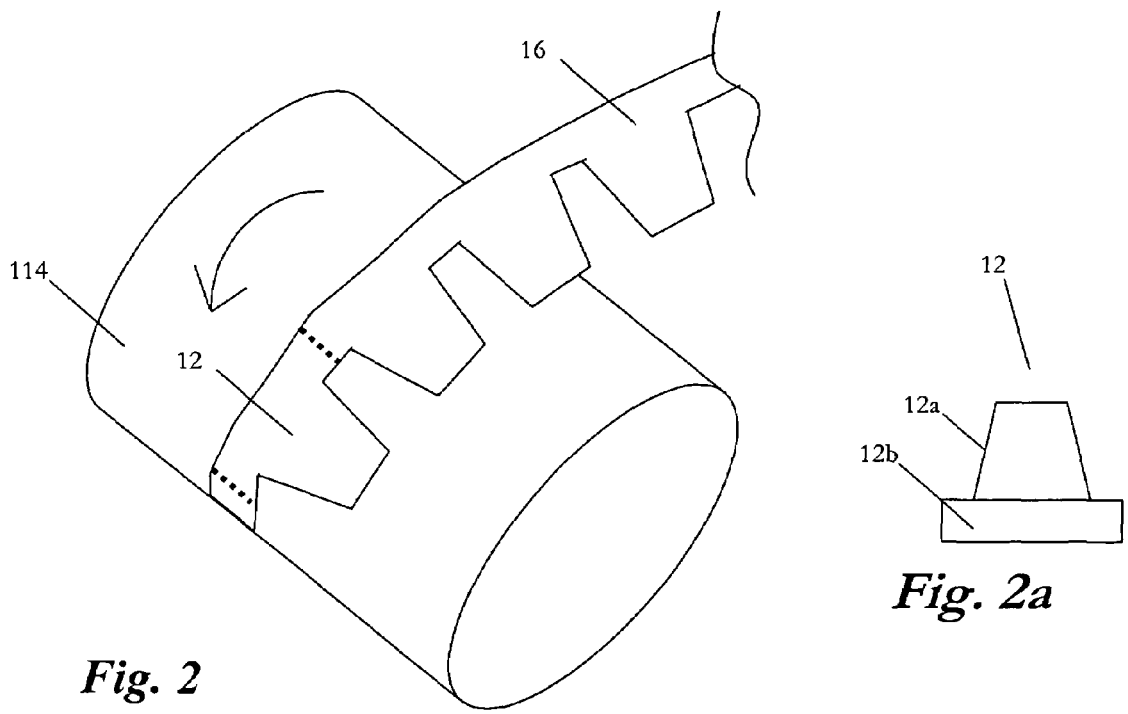
*Fig. 2*
*Fig. 2a*

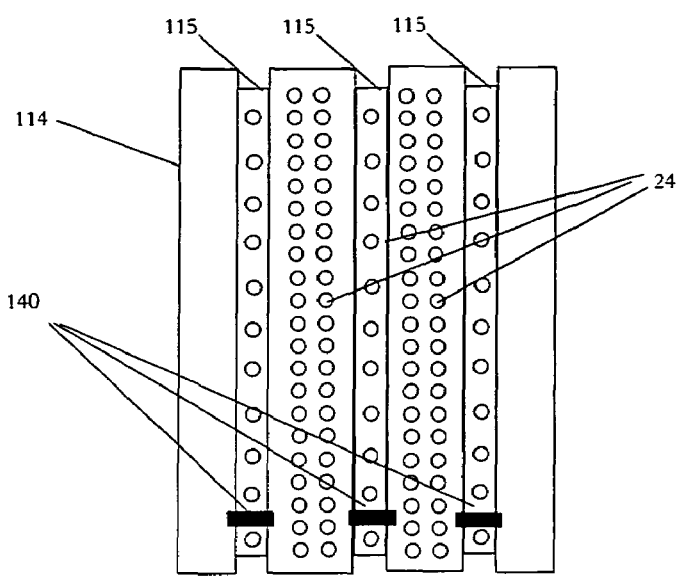
*Fig. 4*
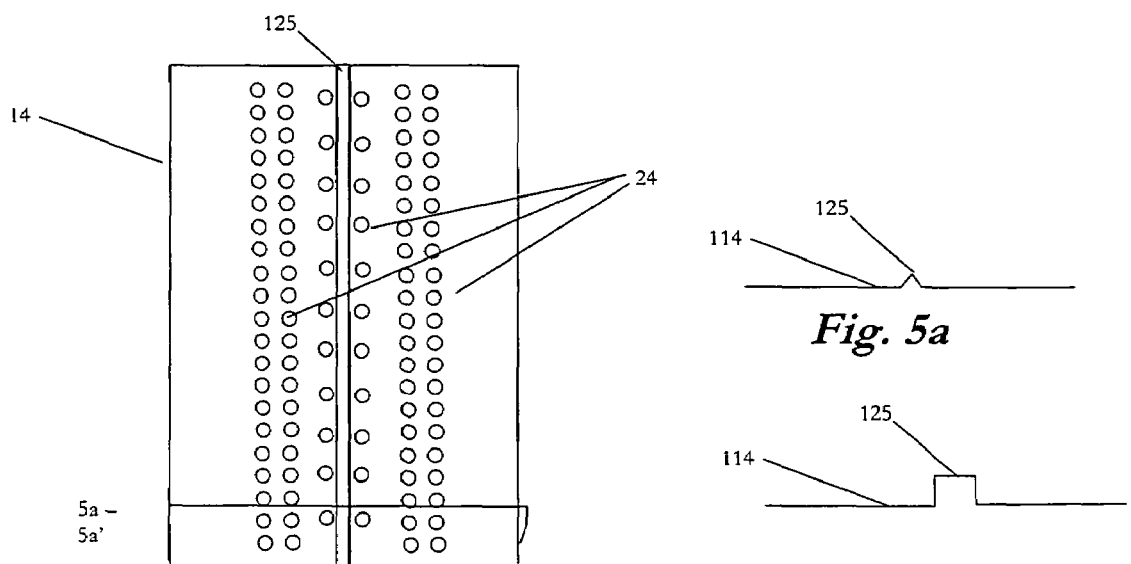
*Fig. 5*
*Fig. 5a*
*Fig. 5b*

WEB STABILIZATION ON A SLIP AND CUT APPLICATOR

BACKGROUND OF THE INVENTION

The present invention relates to disposable undergarments and more specifically, to methods and apparatuses for processing disposable undergarments.

Various types of automatic manufacturing equipment have been developed which produce the desired results with a variety of materials and configurations. This equipment generally includes slip-and-cut applicators to which this invention is principally directed.

This invention is directed primarily at slip-and-cut applicators, which are typically comprised of a cylindrical rotating vacuum anvil; a rotating knife roll; and a transfer device. In typical applications, a tape web or an ear web can be fed along a vacuum face of the rotating anvil. A knife-edge, mounted on the rotating knife roll, cuts subsequent ears from each other against the anvil face. This knife-edge is preferably moving at a surface velocity similar to that of the anvil's circumference. Once cut, the web segment is held by vacuum drawn through holes on the anvil's face as it is carried at the anvil's speed downstream to the transfer point where the web segment is transferred to the traveling web.

A common problem associated with slip-and-cut applicators occurs at the point of cut. Since the web being cut is traveling at a very low velocity compared to the anvil and knife velocity (perhaps 1/20th), the engagement of the knife with the ear web tends to induce a high tensile strain in the ear web. Having been placed under such a high level of stress, the ear web can recoil violently when the cut is finally completed, causing loss of control of the ear web. This "snap-back" effect increases with the thickness of the ear web. Thicker webs tend to prolong the duration of engagement with the knife before completion of the cut, thereby increasing the build-up of strain. This is a common process problem that is usually addressed by the provision of various shock-absorbing devices. One possible solution might have been to reduce the surface velocity of the knife, but substantially different velocities between the knife and anvil result in rapid wear of the knife edge and/or anvil face, depending on relative hardness.

Continual improvements and competitive pressures have incrementally increased the operational speeds of disposable diaper converters. As speeds increased, the mechanical integrity and operational capabilities of the applicators had to be improved accordingly. As a further complication, the complexity of the web segments being attached has also increased.

Slip-and-cut apparatus' are well known for their ability to cut relatively short segments of one web and place them accurately on another, higher speed web. Certain materials, however, behave badly in these applications. The tension pulsation caused by the cutting may cause the material to snap back, losing its natural track down the moving surface of the anvil roll. This is especially common with thick webs. Other materials, such as nonwoven fabrics, may be difficult to control because they are very porous and provide little resistance to air flow to keep the material on track. Still other materials, such as certain perforated films may possess texture qualities which tend to be very unstable on the anvil surface, acting instead like a puck on an air hockey table.

These problems are further exacerbated by using materials with a very low modulus of elasticity. Here, even very low levels of vacuum at the anvil surface may cause the material to stretch with the advancing movement of the anvil. The sudden change of tension seen when the knife cuts this over-stretched web can result in severe snap-back and complete loss of position, relative to the intended centerline. Likewise, webs with very high moduli may snap back violently when the web is cut.

An even more challenging requirement is to control an asymmetrical web, such as a diaper ear web as it passes through the slip-and-cut process. For instance, as described in co-pending application titled "High Speed Vacuum Porting" filed the same day as the present application, the ear web also encounters control difficulties. In such instances, the web has a very narrow continuous ribbon section along one edge, and carries with it a chain of die-cut ears, which must be controlled. This application does not have lines of web tension in the ear section, and while vacuum is generally required to maintain some control of the ears, any excessive draw produced by such vacuum will tend to skew the ear on the anvil as the vacuum-induced drag produced by the faster-moving anvil and felt by the ears is out of line with the ribbon segment.

It is known in the prior art to run a straight web entirely within a groove, such as in commercial embodiments of U.S. Pat. No. 5,407,513. However, this prior art does not provide the desired cross-directional control of webs wider than the groove.

It is therefore, an object of this invention to maintain cross-directional control of the ribbon segment, keeping it parallel to the target web. Likewise, any web that might tend to stray from its natural parallel entry line might benefit from the invention.

SUMMARY OF THE INVENTION

Ears, or wings, are placed on a running web of disposable diapers. Because these webs are often asymmetrical or otherwise incompatible with the principle of slipping over the surface of a moving vacuum roll, the webs may float from side to side or otherwise be drawn out of square by asymmetrical forces. A vacuum groove is provided on a vacuum roll to counter these effects. Alternatively, a ridge with vacuum about the ridge is provided, also to pull a machine direction line of material into the groove or over the ridge, thereby giving the web some degree of cross-directional stability.

In a typical configuration of a slip-and-cut applicator, there is a pattern of vacuum holes distributed to evenly draw the entering web onto the anvil's surface and thence into the cut point where the knife edge engages the anvil. The present invention provides a solution by means of a machine-direction groove along a line of vacuum holes at a place where the main tension lines in the in-feeding material are continuous. This groove, with its vacuum, will draw the web into the groove, thereby provide a degree of axial stiffness and a corresponding obstruction and resistance to cross-directional movement.

Such a groove is normally wider than the diameter of the vacuum holes, which fall into the groove, but is also normally kept narrow and shallow so as to avoid producing a visible wrinkle in the material. A typical width and depth might be 3 mm wide by 1 mm deep. In another embodiment, the anvil may be provided with a series of circumferential grooves, thereby providing the material with a corrugated bed of parallel grooves on which the advancing material may ride.

Still another embodiment achieves similar results by means of a raised ridge, rather than a groove. Such a ridge provides the material with the necessary obstruction and stiffness resistant to cross-directional movement. In such embodiments, vacuum holes are positioned on either side of such a ridge so as to better hold the material against said ridge.

BRIEF DESCRIPTION OF THE DRAWINGS

FIG. 1 is a diagrammatic side view of a Prior Art process;

FIG. 2 is a perspective view of an anvil roll of the present invention carrying an ear web;

FIG. 2a is a an ear carried by the anvil roll of the present invention;

FIG. 4 is a front view of an alternate embodiment of an anvil roll of the present invention;

FIG. 5 is a front view of a second alternate embodiment of an anvil roll of the present invention;

FIG. 5a is a partial cross sectional view of a ridge patter applied on an anvil roll of the present invention.

FIG. 5b is a partial cross sectional view of an alternate ridge pattern of the present invention.

DESCRIPTION OF THE PREFERRED EMBODIMENT

Figures 3, 3A:
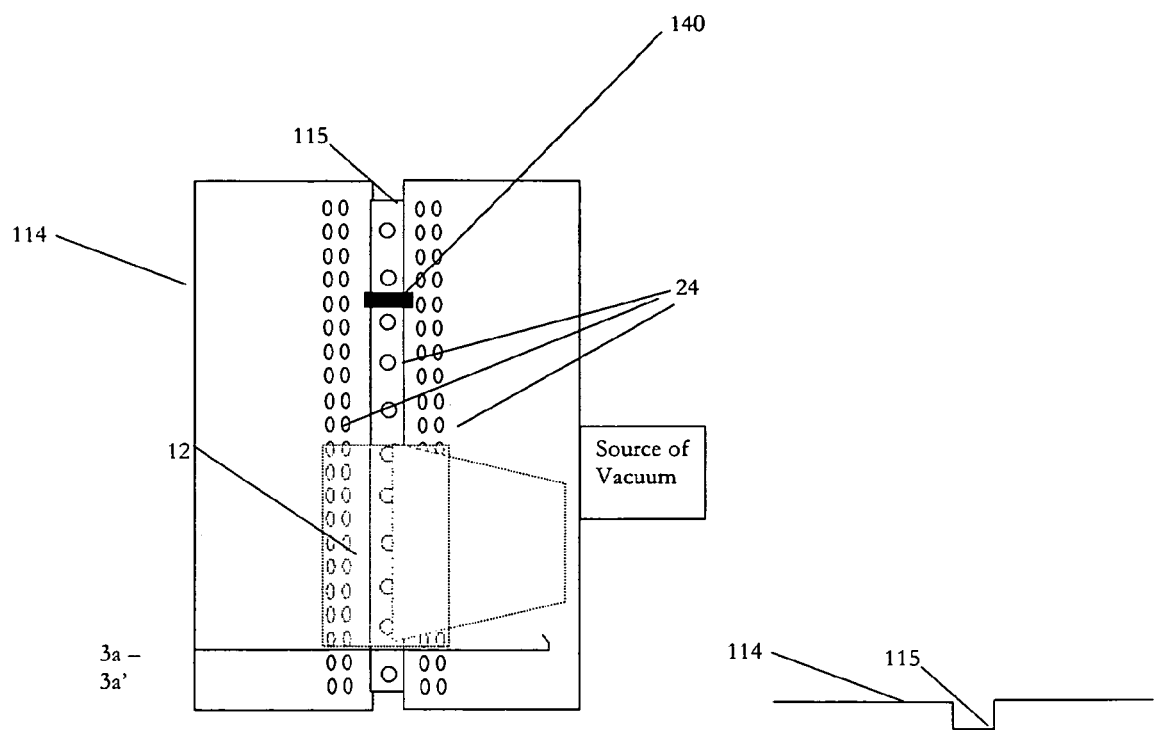
FIG. 3 is a front view of an anvil roll of the present invention.
FIG. 3a is a partial cross sectional view of an anvil roll of the present invention.

Although the disclosure hereof is detailed and exact to enable those skilled in the art to practice the invention, the physical embodiments herein disclosed merely exemplify the invention, which may be embodied in other specific structures. While the preferred embodiment has been described, the details may be changed without departing from the invention.

Referring more particularly to the drawings there is seen in FIG. 1 a diagrammatic illustration of a prior art process for applying tabs to webs in a diaper making process. The present invention can use this prior art method of affixing the tabs 12 to the web 10, with a different anvil, the new anvil 114 described below. Web 10 is a composite material used in formation of diapers which is generally formed of various layers of material such as plastic back sheets, absorbent pads and nonwoven topsheets. A series of ears 12 are applied to web 10. In the illustrated process a rotatable vacuum anvil 14 is used to supply the ears 12 to web 10. Anvil 14 has internally reduced air pressure or vacuum (shown diagrammatically on FIG. 2), and a plurality of openings 24 are provided through its surface to enable suction of the tab segments 12 against the anvil surface 14. A web of the ear tab forming material 16 is fed by rollers 20 and 22 against the anvil surface 14 where it is cut into segments by a rotary knife 18.

In the prior art, the surface of the anvil roll 14 has vacuum holes 24 on its smooth surface. In a typical configuration of a slip-and-cut applicator, there is a pattern of vacuum holes 24 distributed to evenly draw the entering web onto the surface of anvil 14 and thence into the cut point where the knife edge 18 engages the anvil 14.

Referring now to FIG. 2, a perspective view of an anvil roll 114 is shown carrying an ear web, or forming material 16. This material 16 is comprised of two portions, 12a and 12b as shown in FIG. 2a. Segment 12a is more specifically referred to as the tab section of the ear 12, segment 12b is a ribbon section of the ear 12.

The ear forming material 16 is cut into individual ears 12 by the rotary knife 18 as shown in FIG. 1, along lines such as the dashed lines shown in FIG. 2.

Referring now to FIG. 3, a front view of an anvil roll 114 of the present invention is shown carrying an ear 12 in phantom. In this embodiment, a machine-direction groove 115 along a line of vacuum holes 24 is provided at a place where the main tension lines in the in-feeding material such as ear forming material 16 is continuous, such as the ribbon portion 12b. This groove 115, with its vacuum applied through holes 24 as shown, will draw the web into the groove 115, and thereby provide a degree of axial stiffness and a corresponding obstruction and resistance to cross-directional movement. It is preferred that vacuum holes 24 reside both within the groove 115 and outside of the groove 115 on the surface of the anvil roll 114 as shown.

Still referring to FIG. 3, anvil insert 140 is provided across the groove 115 to provide a surface to engage rotary knife 18 at the desired location. Insert 140 creates a bridge for the ribbon 12b to ride upon so that the ribbon 12b can be introduced in a cutting position relative to the knife 18 as the knife 18 is shown in FIG. 1. Alternatively, insert 140 could simply be machined into the roll 114.

Referring now to FIG. 3a, a partial cross sectional view of the anvil roll 114 along line 3a-3a' from FIG. 2 is shown. As can be seen, the groove 115 visible. A preferred embodiment of the groove 115 is that the groove 115 is slightly wider than the diameter of the vacuum holes 24, which fall into the groove 115, but is also normally kept narrow and shallow so as to avoid producing a visible wrinkle in the material. A typical width and depth might be 3 mm wide by 1 mm deep. It is also preferred that the groove 115 be wider than the ribbon 12b of the ears 12.

In operation, the ears 12 are carried by the anvil 114. The ears 12, and preferably the ribbon portion 12b, are passed over the groove 115, and drawn slightly into the groove 115. The vacuum applied to the groove 115 slightly holds the ears 115 along the ribbon 12a of the ears thereby providing stability from either non-machine direction rotation, or non-machine direction pulling or pushing.

Referring now to FIG. 4, a front view of an alternate embodiment of the anvil roll 114 of the present invention is shown. In this embodiment, the anvil 114 is provided with a series of radial grooves 115 in the machine direction, thereby providing the material with a corrugated bed of parallel grooves 115 on which the advancing material (not shown) may ride.

Referring now to FIG. 5, a front view of a second alternate embodiment of the anvil roll 114 of the present invention is shown. This embodiment achieves the desired obstruction and stiffness resistant to cross-directional movement by means of a raised ridge 125 (or series of ridges 125, not shown), rather than a groove 115. The ridge 115 is provided with vacuum holes 24 that are positioned on either side of the ridge 125 so as to better hold the material against said ridge 125.

Referring now to FIG. 5a, a partial cross sectional view of the anvil roll 114 along line 5a-5a' from FIG. 4 is shown. As can be seen, the ridge 125 is visible. In this embodiment, the ridge 125 provides a spine about which cross-directional stability is added to the advancing ribbon.

Referring now to FIG. 5b, a partial cross sectional view of an alternate ridge pattern 125 is shown. In this embodiment, the ridge 125 may be dimensioned similarly to the groove 115 described previously.

In operation, similar to that described with the groove system above, the die-cut ears are applied the moving web, also similar to that shown in FIG. 1. The ears are passed on top of the ridge 125, and drawn about the ridge 125 slightly by the vacuum holes provided near to the sides of the ridge 125. This vacuum along a length of the ears thereby also provides stability from either non-machine direction rotation, or non-machine direction pulling or pushing, similar to that described with the groove system and method above.

It can be seen that either the ridge or the groove/vacuum system described above can comprise means for maintaining cross-directional stability in an advancing in-feeding web, because the in-feeding web will be provided with a degree of resistance from non-machine directional movement by the slight fixation to the machine direction vacuum holes 24.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention.

I claim:

1. An anvil roll comprising:
   a substantially cylindrical anvil body, said anvil body having a generally curviplanar outer surface,
   at least one groove provided on said anvil body, said at least one groove extending through said outer surface of the anvil body, said at least one groove oriented in a machine direction,
   a source of vacuum coupled to said anvil body;
   a first plurality of vacuum holes provided on said outer surface of said anvil body, said first set of vacuum holes being outside of every at least one groove, said first plurality of holes communicative with said source of vacuum;
   a second plurality of vacuum holes provided in at least one of said at least one groove, said second plurality of holes communicative with said source of vacuum;
   an advancing in-feeding web positioned across said at least one groove, a portion of said web drawn into said at least one groove to provide the cross-directional stability.

2. An anvil roll according to claim 1, the anvil roll further comprising an insert across said at least one groove for engaging a cutting structure.

3. An anvil roll according to claim 1, said anvil roll further comprising an integral cutting surface across said at least one groove.

4. An anvil roll comprising:
   a substantially cylindrical anvil body;
   a source of vacuum coupled to said anvil body;
   a plurality of vacuum holes provided on an outer surface of said anvil body, said holes communicative with said source of vacuum;
   a ridge extending outwardly from said outer surface of said anvil body, said ridge oriented in a machine direction;
   a plurality of vacuum holes provided proximally to said ridge, wherein at least one vacuum hole is provided on a first lateral side of said ridge and at least one vacuum hole is provided on a second lateral side of said ridge;
   an advancing in-feeding web positioned across said ridge, a portion of said web drawn over said ridge to provide the cross-directional stability.

5. A method of applying ribbon to a moving web, said method comprising:
   providing an anvil roll with at least one ridge, said ridge extending outwardly from the outer surface of the anvil roll;
   applying vacuum to the surface of the anvil roll on a first lateral side and a second lateral side of said ridge;
   passing an advancing ribbon about said ridge;
   passing said ribbon about said ridge and over said vacuum;
   whereby said vacuum and said ridge provide cross-directional stability to said advancing ribbon.

* * * * *